(12) United States Patent
Massengale et al.

(10) Patent No.: US 9,254,146 B2
(45) Date of Patent: Feb. 9, 2016

(54) ECHOGENIC NERVE BLOCK APPARATUS AND SYSTEM

(75) Inventors: Roger Dillard Massengale, Mission Viejo, CA (US); Steve S. Khalaj, Laguna Hills, CA (US); Siddharth Desai, Ladera Beach, CA (US); Dominic J. Cooke, Mission Viejo, CA (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 13/272,643

(22) Filed: Oct. 13, 2011

(65) Prior Publication Data

US 2012/0095404 A1 Apr. 19, 2012

Related U.S. Application Data

(60) Provisional application No. 61/394,040, filed on Oct. 18, 2010.

(51) Int. Cl.
*A61M 5/00* (2006.01)
*A61B 17/34* (2006.01)
*A61M 19/00* (2006.01)
*A61B 8/08* (2006.01)
*A61B 19/00* (2006.01)
*A61M 5/32* (2006.01)

(52) U.S. Cl.
CPC ............ *A61B 17/3401* (2013.01); *A61M 19/00* (2013.01); *A61B 8/0841* (2013.01); *A61B 2017/3413* (2013.01); *A61B 2019/5425* (2013.01); *A61B 2019/5429* (2013.01); *A61M 5/3286* (2013.01); *A61M 5/3291* (2013.01)

(58) Field of Classification Search
CPC . A61M 5/3286; A61M 5/3291; A61M 19/00; A61B 8/0841; A61B 17/3401; A61B 2017/3413; A61B 2019/5425; A61B 2019/5429
USPC .................................... 604/158, 164.01, 272
See application file for complete search history.

(56) References Cited

U.S. PATENT DOCUMENTS

| 4,401,124 | A | | 8/1983 | Guess et al. |
| 5,081,997 | A | * | 1/1992 | Bosley et al. ................. 600/458 |
| 5,201,314 | A | | 4/1993 | Bosley, Jr. et al. |
| 5,289,381 | A | | 2/1994 | Demuth et al. |

(Continued)

OTHER PUBLICATIONS

Office Action—Russian Patent Office, Jul. 30, 2015.

(Continued)

*Primary Examiner* — Theodore Stigell
(74) *Attorney, Agent, or Firm* — Dority & Manning, P.A.

(57) ABSTRACT

An apparatus for performing a nerve block procedure, the apparatus being composed of an echogenic needle or an echogenic soft tissue tunneling device and an echogenic catheter configured for controlled delivery of a medication. The apparatus may further include a sheath such that at least one of the needle or tunneling device and sheath is echogenic. The present invention also encompasses a system for performing a nerve block procedure, the system includes introducing an echogenic needle in the general area of a nerve bundle, positioning the echogenic needle adjacent the nerve bundle utilizing sonic imaging techniques, introducing an echogenic catheter configured for controlled delivery of a fluid through the echogenic needle, withdrawing the echogenic needle, positioning the echogenic catheter adjacent the nerve bundle utilizing sonic imaging techniques, and delivering fluid to the nerve bundle through the echogenic catheter.

11 Claims, 11 Drawing Sheets

(56) References Cited

U.S. PATENT DOCUMENTS

| | | | |
|---|---|---|---|
| 5,327,891 | A | 7/1994 | Rammler |
| 5,643,197 | A * | 7/1997 | Brucker et al. ............. 604/20 |
| 6,018,676 | A * | 1/2000 | Davis et al. ............. 600/431 |
| 6,592,612 | B1 * | 7/2003 | Samson et al. ............. 607/105 |
| 6,770,070 | B1 * | 8/2004 | Balbierz ............. 606/41 |
| 7,004,923 | B2 * | 2/2006 | Deniega et al. ............. 604/4.01 |
| 7,547,302 | B2 | 6/2009 | Porto et al. |
| 8,285,362 | B2 | 10/2012 | Dietz et al. |
| 2003/0158480 | A1 | 8/2003 | Tornes et al. |
| 2003/0181887 | A1 | 9/2003 | Castillo Deniega et al. |
| 2007/0179508 | A1 | 8/2007 | Arndt |
| 2008/0058702 | A1 * | 3/2008 | Arndt et al. ............. 604/20 |
| 2008/0086161 | A1 | 4/2008 | Massengale et al. |
| 2008/0154136 | A1 * | 6/2008 | Webler ............. 600/463 |
| 2008/0200874 | A1 * | 8/2008 | Ferry ............. 604/103.1 |
| 2008/0287939 | A1 * | 11/2008 | Appling et al. ............. 606/15 |
| 2009/0030307 | A1 | 1/2009 | Govari et al. |
| 2009/0227962 | A1 * | 9/2009 | Eversull et al. ............. 604/265 |
| 2010/0082035 | A1 | 4/2010 | Keefer |
| 2011/0172542 | A1 | 7/2011 | Racz |

OTHER PUBLICATIONS

Translation of Office Action—Japanese Patent Office, Aug. 18, 2015.

* cited by examiner

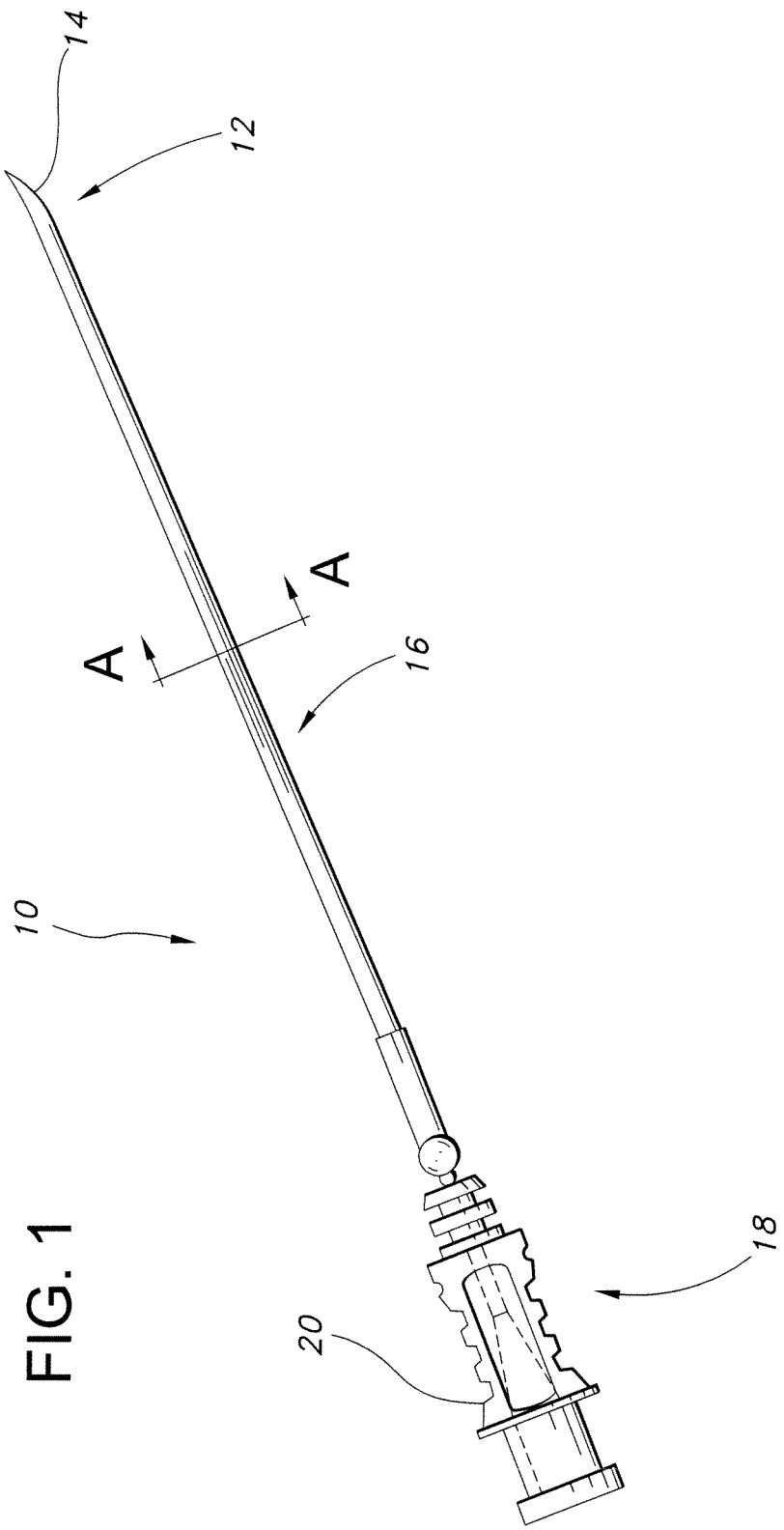

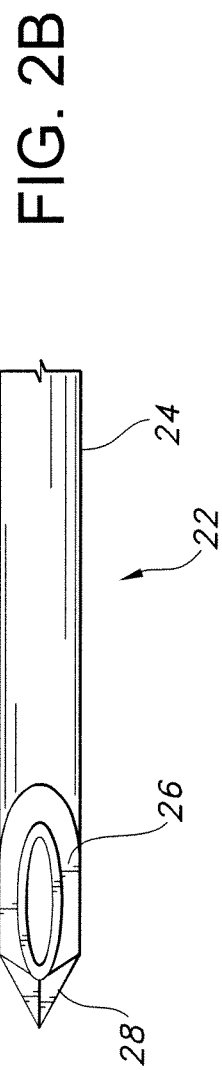
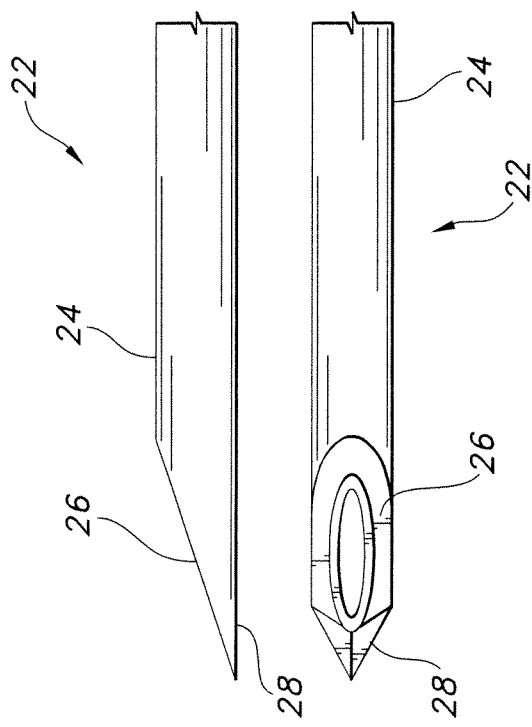
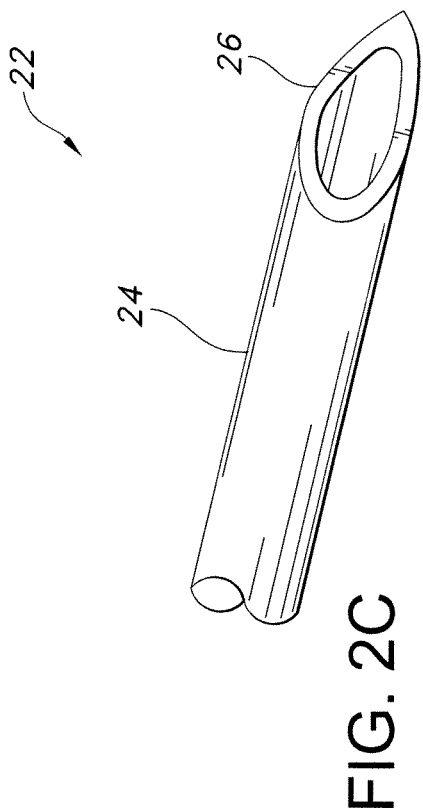
FIG. 2A
FIG. 2B
FIG. 2C

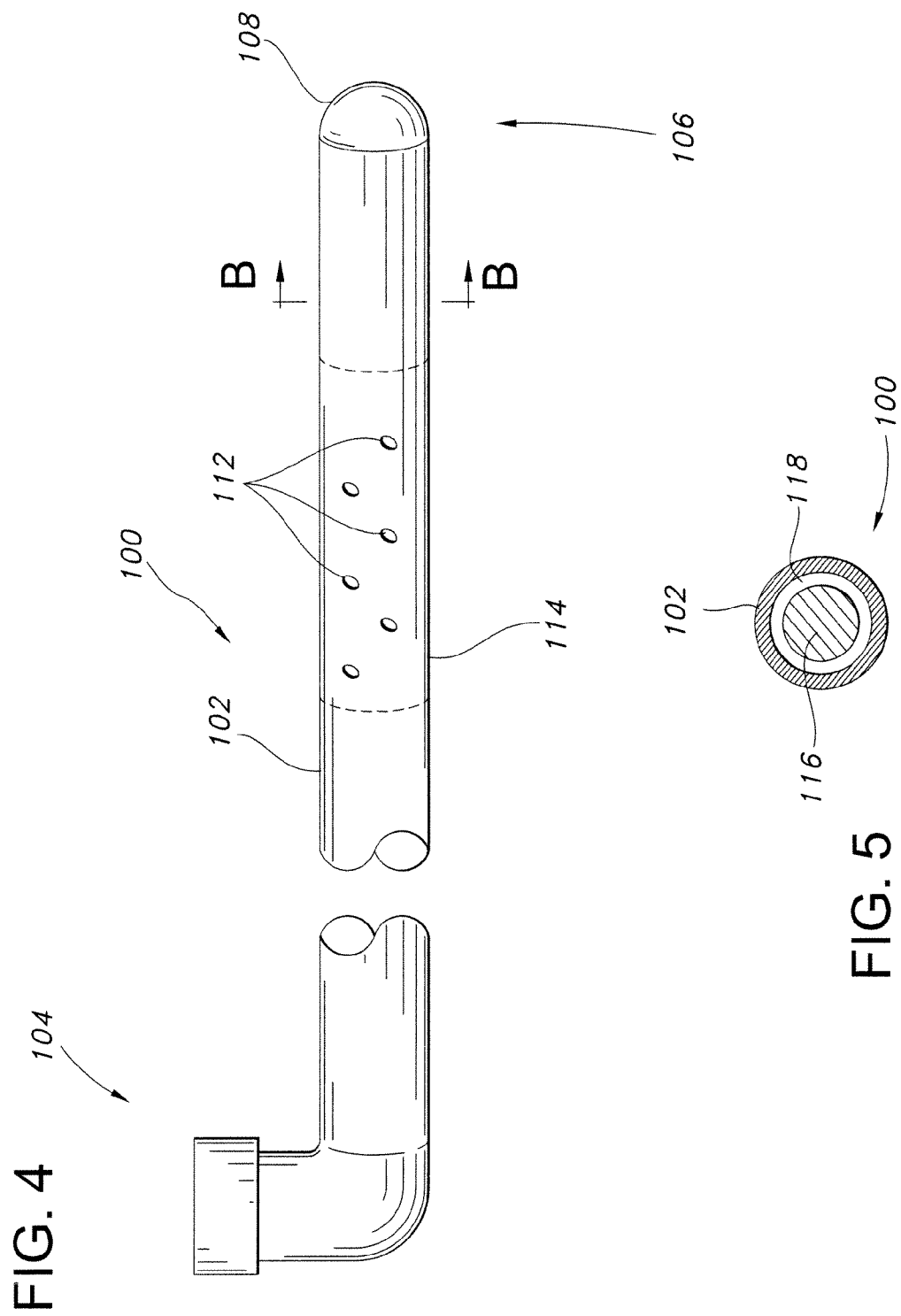

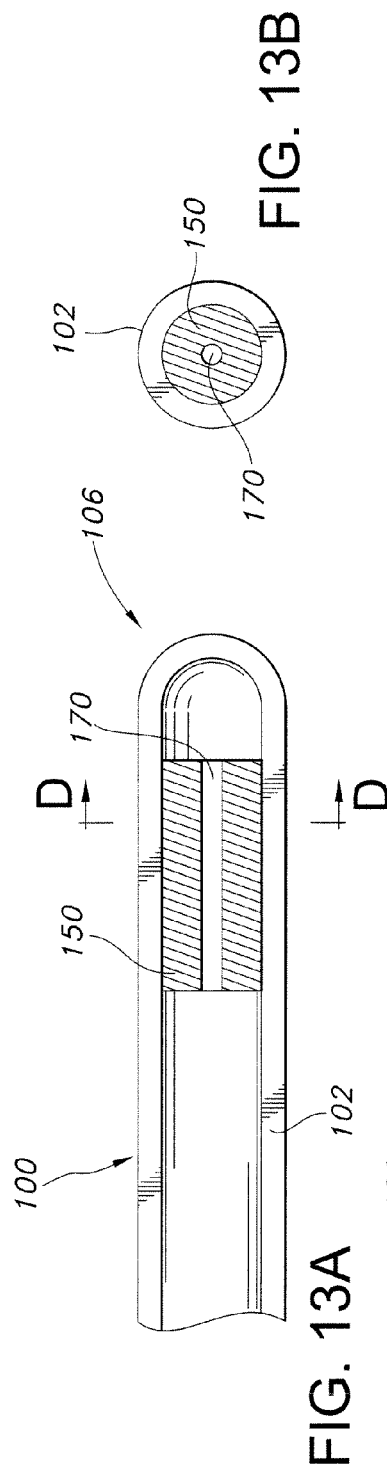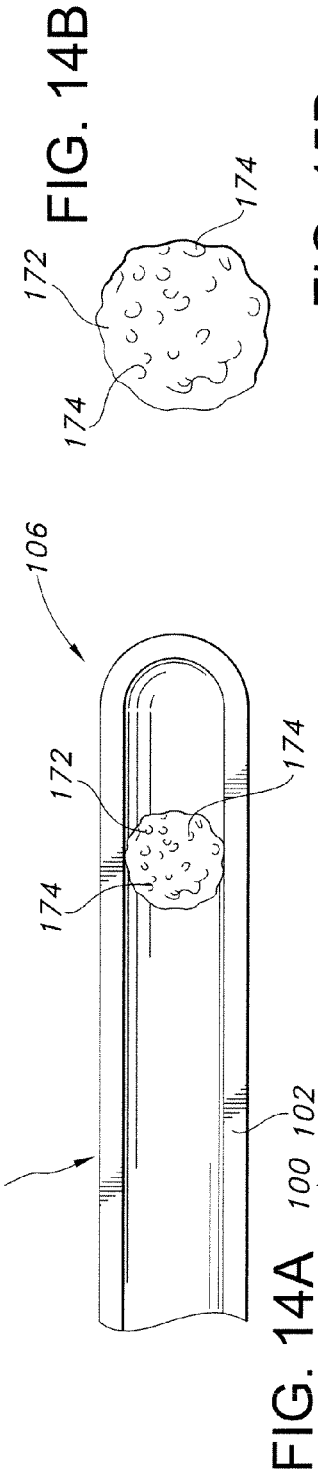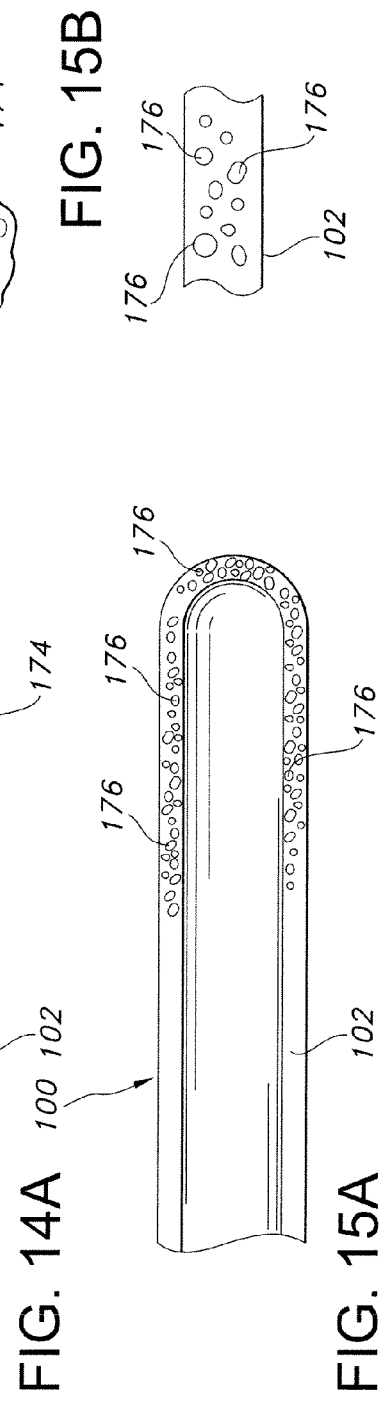

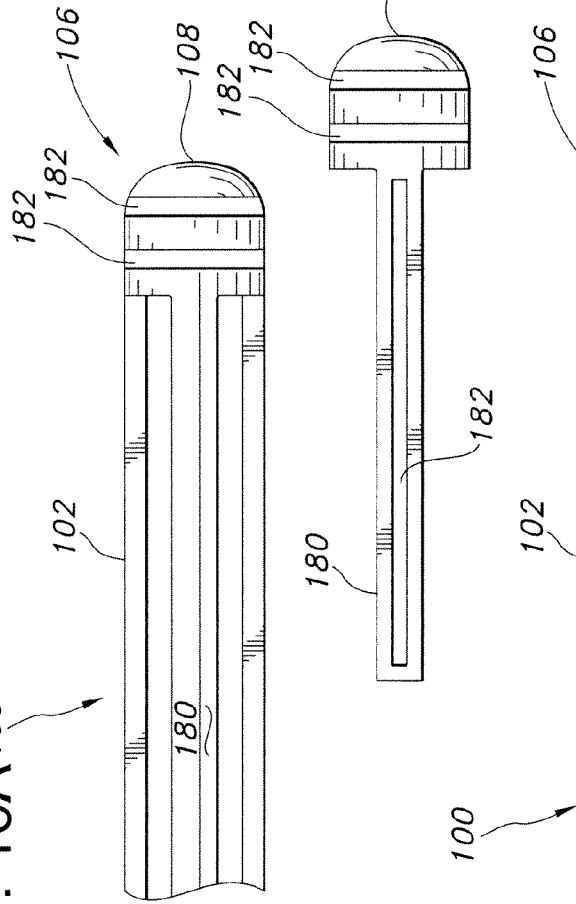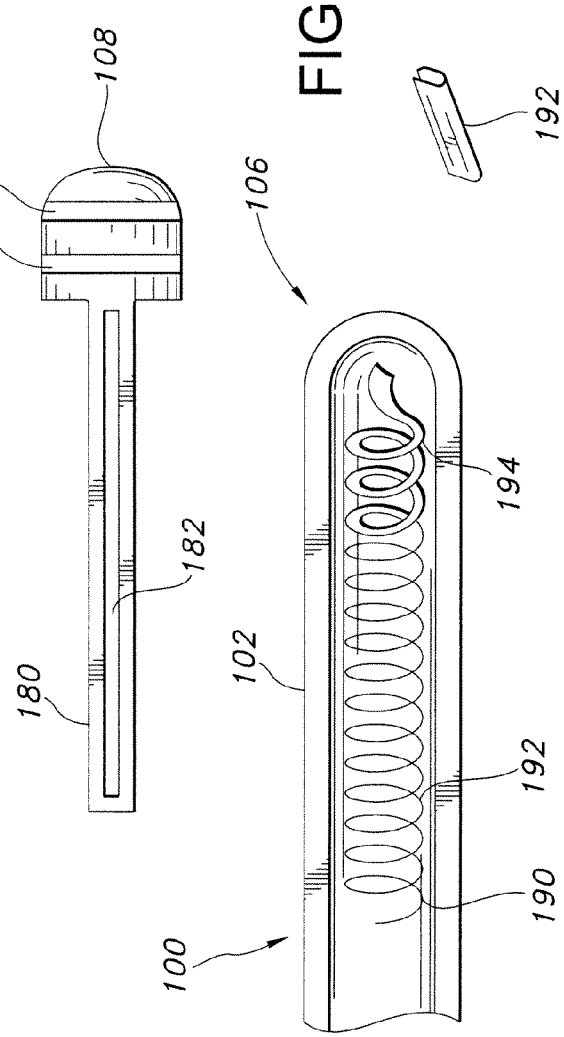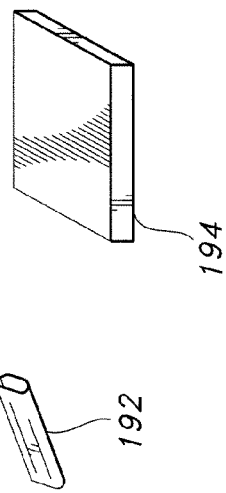

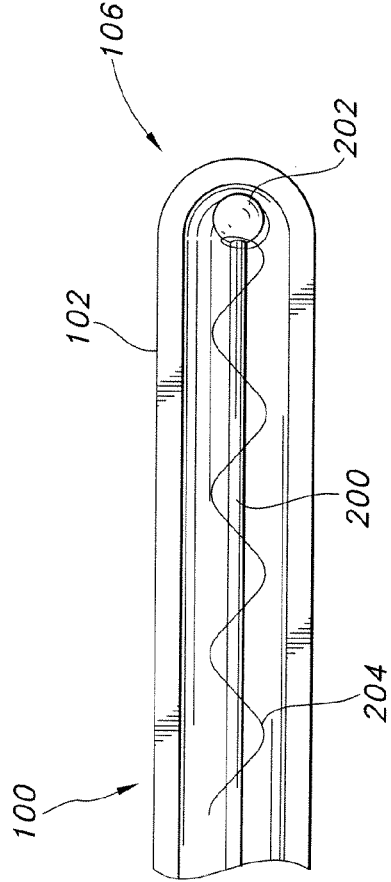
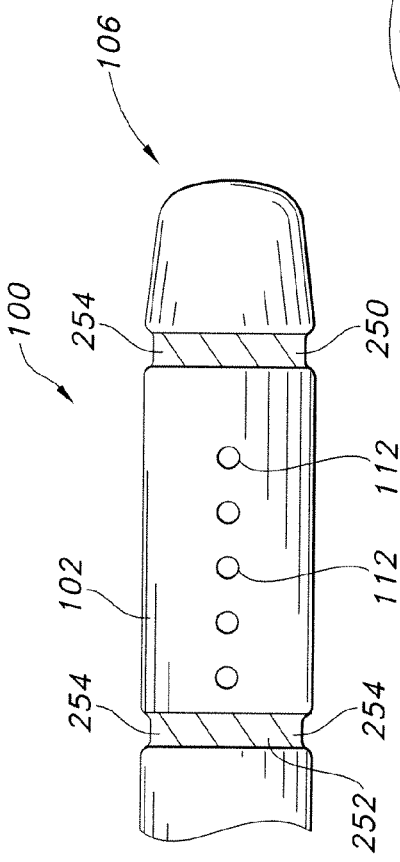
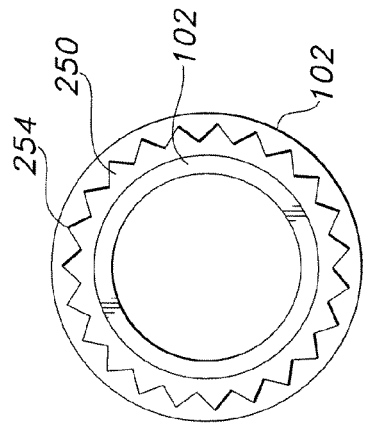

ECHOGENIC NERVE BLOCK APPARATUS AND SYSTEM

This application claims the benefit of priority from U.S. Provisional Application No. 61/394,040 filed on Oct. 18, 2010, the contents of which are incorporated herein by reference.

FIELD OF THE INVENTION

This invention relates to pain management systems, and more specifically to catheter-based infusion systems for the administration of fluids. Most specifically, this invention relates to an apparatus and system for performing a nerve block procedure.

BACKGROUND OF THE INVENTION

Prior to performing a surgical operation on a part of the body, such as for example the arms or legs, it may be desirable to perform a nerve block in order to anesthetize a nerve bundle in a part of the body proximate to where surgery will occur. Often, a catheter-based infusion system is utilized to both block the nerve bundle for surgery and to provide a continuous, low flow rate of the anesthetic over a period of time (e.g., 2-3 days following surgery) for post-operative pain management.

One approach is to introduce an epidural-type needle or needle and peel-away-type sheath into the general area of the desired nerve bundle. Once proper location of the needle is achieved, a test dose of the anesthetic may be provided through the epidural needle and a catheter may be introduced through the needle to administer the anesthetic and maintain the nerve block.

Several methods of targeting needle location exist today—insulated needles having an integral conductive wire such that a small amount of current may be pulsed through the needle or catheter by a nerve stimulator (i.e., a current generator). An electrical current of 0.1 to about 2 mA will induce motor movement in the patient when the tip of the needle (frequently called a "stimulating needle") is near the nerve. When the stimulating needle is probed into the general area of the desired nerve bundle, the pulsing current stimulates the nerve and causes a motor response to assist in properly locating the needle. As the current is reduced, the motor effect is also reduced so a needle that causes movement at a low current is likely to be very close to the desired area for drug delivery.

One problem with this approach is that the catheter insertion through the needle may move the tip of the needle away from the target zone. Alternatively and/or additionally, the tip of the catheter may curl away from the target zone during insertion.

Several manufacturers have designed stimulating catheters that correct this problem by passing the current first through the needle and then separately through the catheter. The problem with this is that the catheter cannot be steered to the target zone without risking pulling back through the needle and potentially damaging the catheter. In addition, the additional time needle to place and maneuver the catheter is significant and after the catheter is secured, it can dislodge by patient movement and then become ineffective.

Ultrasound guided techniques have added imaging to the procedure, but they are mainly used to see the adjacent vessels and are not always good at seeing the needle and/or catheter. The problem with ultrasound guided techniques is that the needle and catheter cannot be easily seen through tissue. That is, the ability to see the tip and/or other portions of the needle and/or catheter under ultrasound imaging techniques is limited. Another problem is that conventional catheters do not allow one to place the catheter quickly allowing for some small migration or tip mis-positioning while still delivering drug to the target area.

A variety of approaches have been used to enhance ultrasonic imaging of medical devices by increasing the acoustic reflection coefficient of the devices. In U.S. Pat. No. 4,401,124 issued to Guess et al., the reflection coefficient of a biopsy needle is enhanced by the use of a diffraction grating disposed on the surface of the needle. A variety of mechanisms for enhancing the ultrasound image of a portion of a medical instrument are also disclosed in U.S. Pat. No. 5,289,831 issued to Bosley, U.S. Pat. No. 5,201,314 issued to Bosley et al. and U.S. Pat. No. 5,081,997, also issued to Bosley et al. These patents disclose catheters and other devices provided with echogenic surfaces including spherical indentations or projections in the range of 0.5 to 100 microns or fabricated of material incorporating glass spheres or high density metal particles in the range of 0.5 to 100 microns. The use of micro-bubbles introduced into polymers to provide echogenic catheter components is described in U.S. Pat. No. 5,327,891, issued to Rammler.

However, these features add complexity to manufacturing and may negatively impact the performance of a catheter having a plurality of exit holes along a portion of the catheter. For example, glass beads adhered to the exterior of a catheter may become dislodged. Glass beads incorporated into the polymer matrix may create difficulties during creation of exit holes. Microbubbles formed in the polymer matrix of the catheter wall can be difficult to form reliably during the extrusion process. Spherical indentations or spherical protuberances can be challenging and/or expensive to form on a single use item. For example, an EchoTip® Ultrasound Needle has a plurality of spherical indentations that can increase acoustic reflection. However, these spherical indentations can be difficult or expensive to produce in a metal needle and may be ineffective when implemented in items that are generally not very acoustically reflective such as, for example, a polymer catheter.

SUMMARY OF THE INVENTION

The present invention addresses these problems by providing an apparatus for performing a nerve block procedure, the apparatus being composed of an echogenic needle and an echogenic catheter configured for controlled delivery of a medication.

The present invention also encompasses a system for performing a nerve block procedure, the system includes introducing an echogenic needle in the general area of a nerve bundle, positioning the echogenic needle adjacent the nerve bundle utilizing sonic imaging techniques, introducing an echogenic catheter configured for controlled delivery of a fluid through the echogenic needle, withdrawing the echogenic needle, positioning the echogenic catheter adjacent the nerve bundle utilizing sonic imaging techniques, and delivering fluid to the nerve bundle through the echogenic catheter.

An aspect of the present invention encompasses addresses an echogenic needle configured for placement into the body adjacent a nerve bundle. The echogenic needle has a distal end composed of an echogenic needle tip, a hollow needle body, and a proximal end that includes a fitting. The needle body may be an echogenic needle body.

Generally speaking, the echogenic needle tip may be formed from cobalt chromium (also referred to as "cobalt chrome"), glass or other material having a high degree of acoustic impedance. Alternatively and/or additionally, the echogenic needle tip may have a shape or spatial configuration that reflects an effective amount of acoustic waves so the tip is satisfactorily visible during sonic imaging. Suitable shapes for the echogenic needle tip include beveled, generally planar surfaces. Alternatively and/or additionally, grooves and/or indentations may be added to the needle.

The needle tip and/or the needle body may be rendered echogenic by coating the needle tip and/or a surface of the needle body with a material that increases acoustic impedance. Exemplary materials include titanium carbide, titanium nitride, titanium aluminum nitride, titanium aluminum carbon nitride and similar materials. Hard, dense, amorphous non-crystalline solids such as glass, acrylic glass—also referred to as poly(methyl methacrylate), and hard, glassy hydrogels such as those described in US Patent Application Publication No. US 2006/0141186 may also be used. The needle tip and/or needle body may be rendered echogenic by coating the needle tip and/or a surface of the needle body with various known echogenic coatings.

Another aspect of the present invention encompasses an echogenic catheter configured for controlled delivery of a fluid across an anatomical region. The echogenic catheter is composed of an elongated tubular member and an echogenic catheter tip. The elongated tubular member may be an elongated tube with a plurality of exit holes or slots in a portion of the elongated tube, and an elongated porous member residing within the tube. Alternatively, the elongated tubular member may be made of a porous membrane such as a filtration membrane. Exemplary filtration membranes may be made of polytetrafluoroethylene.

The echogenic catheter tip may be a portion of a distal end of the catheter formed from cobalt chrome, glass, or other material having a high degree of acoustic impedance. Alternatively and/or additionally, the echogenic catheter tip may be or may include an echogenic insert or plug formed from or coated with cobalt chrome, glass, or other material having a high degree of acoustic impedance. The echogenic catheter tip, insert or plug may have a shape or spatial configuration that reflects an effective amount of acoustic waves so the tip is satisfactorily visible during sonic imaging. Suitable shapes include gear shapes (e.g., circular or cylindrical shapes having grooves, notches and/or crenulations that provide a plurality of flat reflective surfaces), spherical shapes, multi-faceted geometric shapes formed by interlocking polygons (e.g., a geodesic dome shape). Sharp and/or flat edges of the echogenic insert may engage the walls of the lumen defined by the catheter body to prevent the echogenic insert from moving relative to the elongated tubular member.

The elongated tubular member of the catheter (and/or the catheter tip) may be rendered echogenic by coating an internal or external surface with a material that increases its acoustic impedance. Exemplary materials include titanium carbide, titanium nitride, titanium aluminum nitride, titanium aluminum carbon nitride and similar materials. Hard, dense, amorphous non-crystalline solids such as glass, acrylic glass— also referred to as poly(methyl methacrylate, and hard, glassy hydrogels such as those described in US Patent Application Publication No. US 2006/0141186 may also be used. The elongated tubular member (and/or the catheter tip) may be rendered echogenic by coating it with various known echogenic coatings.

The coating may be on the outside of the elongated tubular member or the coating may be located on the interior of the elongated tubular member. In some aspects of the invention, the coating on the interior of the elongated tubular member may be a coating that incorporates acoustically reflective particles in a carrier. For example, the coating may include spherical beads of glass or other acoustically reflective material in a carrier that binds spherical beads to an internal surface of the elongated tubular member.

According to another aspect of the invention, the elongated tubular member of the catheter may be rendered echogenic by including an internal component that increases its acoustic impedance. The internal component may be an elongated tubular coil spring enclosed within the tubular member. The elongated tubular coil spring may be may formed from an echogenic material, may be coated with a material that increases its acoustic impedance, or may have a surface that is modified with grooves, diffraction gratings, flattened portions, dimples or the like to increase its acoustic impedance. Alternatively and/or additionally, the internal component may be a component that actively generates acoustic waves that are visible during sonic imaging. Such a component may include an energy source and a transducer such as, for example a piezoelectric transducer that converts the energy into acoustic waves.

In embodiments where the elongated tubular member is an elongated tube with a plurality of exit holes or slots in a portion of the elongated tube and an elongated porous member resides within the tube, it is contemplated that the elongated porous member may be made of or may include material that increases its acoustic impedance.

Other objects, advantages and applications of the present disclosure will be made clear by the following detailed description of a preferred embodiment of the disclosure and the accompanying drawings wherein reference numerals refer to like or equivalent structures.

DESCRIPTION OF THE DRAWINGS

FIG. 1 is an illustration of an exemplary echogenic needle.

FIGS. 2A to 2D are illustrations of illustrated exemplary shapes for increasing the acoustic impedance of a needle tip.

FIG. 4 is an illustration of an exemplary echogenic catheter.

FIG. 5 is an illustration of cross-section of the exemplary echogenic catheter of FIG. 4 taken across line B-B.

FIG. 13A is an illustration of an exemplary echogenic catheter showing an exemplary echogenic insert or plug.

FIG. 13B is an illustration of a cross-section of the exemplary echogenic catheter of FIG. 13A taken across line D-D.

FIG. 14A is an illustration of an exemplary echogenic catheter incorporating an exemplary echogenic bead.

FIG. 14B is an illustration showing a detail of an exemplary echogenic bead from FIG. 14A.

FIG. 15A is an illustration of an exemplary echogenic catheter incorporating voids or bubbles in the catheter.

FIG. 15B is an illustration showing a detail of the echogenic catheter from FIG. 15A.

FIG. 16A is an illustration of an exemplary echogenic catheter incorporating a catheter having an elongated shaft.

FIG. 16B is an illustration showing a detail of the echogenic catheter from FIG. 16A.

FIGS. 17A to 17C are illustrations of an exemplary echogenic catheter incorporating a spring.

FIG. 18 is an illustration of an exemplary echogenic catheter incorporating a guide wire.

FIG. 19 is an illustration of an exemplary echogenic catheter incorporating a metal band.

FIG. 20 is an illustration showing a cross-section of the catheter incorporating a metal band from FIG. 19.

DETAILED DESCRIPTION

Figure 2D:
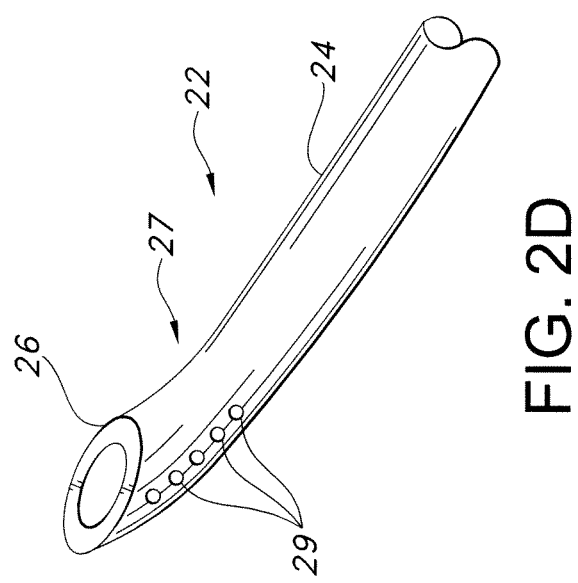
Figure 3:
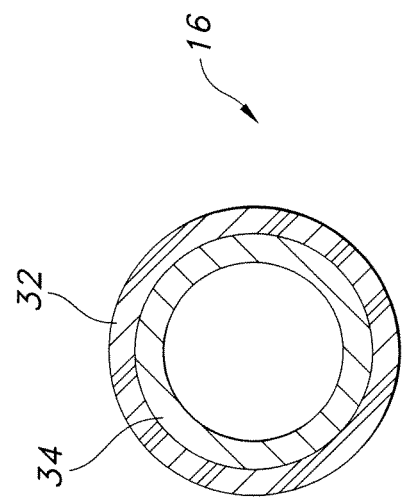
FIG. 3 is an illustration of cross-section of the exemplary echogenic needle of FIG. 1 taken across line A-A.

FIGS. 1-3 illustrate aspects of an exemplary echogenic needle configured for placement into the body adjacent a nerve bundle. Referring to FIG. 1 the echogenic needle 10 has a distal end 12 composed of an echogenic needle tip 14 that may terminate in a beveled aperture having include beveled, generally planar surfaces to enhance acoustic impedance. Examples of needles having such surfaces include, but are not limited to, PAJUNK needles or QUINCKE needles. The echogenic needle 10 further has a hollow needle body 16, and a proximal end 18 that may include a conventional fitting 20.

For example, the echogenic needle may generally have the configuration of a conventional TUOHY needle except for the echogenic features described herein. A suitable needle may be an 18 gauge, steel TUOHY needle with a HUBER tip and a TUOHY hub. Such TUOHY needles are commercially available, with a non-insulated tip and a plastic hub as respective integral portions of the needle. Such TUOHY needles are available in various lengths. The needle may also be a WEISS epidural needle having fixed wings.

Generally speaking, the echogenic needle tip may be formed from or coated with cobalt chromium (also referred to as "cobalt chrome"), glass or other material having a high degree of acoustic impedance. Alternatively and/or additionally, the echogenic needle tip may have a shape or spatial configuration that reflects an effective amount of acoustic waves so the tip is satisfactorily visible during sonic imaging.

Referring now to FIGS. 2A, 2B and 2C, there are illustrated exemplary shapes for increasing the acoustic impedance of a needle tip. FIG. 2A is a side view of an exemplary needle 22 in which a needle body or shaft 24 terminates in a generally flat, planar surface 26. An additional planar surface 28 can be seen at the very tip of the needle. FIG. 2B is an illustration showing a top view of the needle shown in FIG. 2A. In this illustration, needle body or shaft 24 terminates in a generally flat, planar surface 26 which provides surface area to enhance reflection of sonic energy. Additional planar surfaces 28 can be seen at the very tip of the needle. The needle illustrated in FIGS. 2A and 2B is sometimes referred to as a QUINCKE needle or a needle having a QUINCKE-type point. FIG. 2C is an illustration of an exemplary needle 22 in which a needle body or shaft 24 terminates in a generally flat, planar surface 26 which provides surface area to enhance reflection of sonic energy. The needle illustrated in FIG. 2C is sometimes referred to as a PAJUNK needle or a needle having a PAJUNK-type point.

A useful embodiment of a needle is a WEISS epidural needle. In particular, the needle may be a WEISS epidural needle supplied by Becton Dickinson (BD) having fixed wings and a modified TUOHY point. The needle may be a five-inch, 18 gauge needle and is identified by the BD product number 405190. It should be appreciated, however, that other types of suitable epidural needles may also be utilized.

The needle tip and/or the needle body may be rendered echogenic by coating the needle tip and/or a surface of the needle body with a material that increases acoustic impedance. FIG. 3 illustrates a cross-section of the hollow needle body 16 taken along line A-A in FIG. 1. As can be seen in FIG. 3, a coating 32 is applied over the needle body 34. Generally speaking, the coating can be applied over only the needle tip and/or over portions of the needle body (e.g., bands). The coating may be applied by mask and dip techniques. The coating thickness may vary depending on the coating material and its effectiveness at increasing acoustic impedance. For example, the coating may be 1 micrometer in thickness.

Exemplary materials that may be used to coat the needle body 16 include titanium carbide, titanium nitride, titanium aluminum nitride, titanium aluminum carbon nitride, or similar materials may be used. Hard, dense, amorphous non-crystalline solids such as glass, acrylic glass—also referred to as poly(methyl methacrylate), and hard, glassy hydrogels such as those described in US Patent Application Publication No. US 2006/0141186 published Jun. 29, 2006 by Janssen et al. for "Gloves With Hydrogel Coating For Damp Hand Donning and Method of Making Same" may also be used. The needle tip and/or needle body may be rendered echogenic by coating the needle tip and/or a surface of the needle body with various known echogenic coatings such as described in U.S. Pat. No. 6,506,156 issued Jan. 14, 2003 to Jones et al. for "Echogenic Coating"; U.S. Pat. No. 7,229,413, issued Jun. 12, 2007 to Violante et al. for "Echogenic Coatings With Overcoat"; and in U.S. Patent Application Publication No. US 2009/0318746 A1, published Dec. 24, 2009 to Thurmond, II et al. for "Lubricious Echogenic Coatings", the contents of which are incorporated by reference.

Referring now to FIG. 2D, there is illustrated in perspective view a detail of an exemplary needle 22 that is rendered echogenic by joining or incorporating echogenic elements 29 at or near the very tip of the needle. The needle 22 has a needle body or shaft 24 that terminates in a generally flat, planar surface 26. In this particular example, the needle has a slight curve or bends 27 near the tip of the needle that defines the flat planar surface 26. The echogenic elements 29 may be glass beads, spherical particles, grooves, indentations or other features that do not interfere with the function of the needle. The needle illustrated in FIG. 2D is sometimes referred to as a TUOHY needle or a needle having a TUOHY-type point.

FIGS. 4-11 illustrate aspects of an exemplary echogenic catheter. While the catheter may desirably be configured for controlled delivery of a fluid across an anatomical region, the catheter may be configured for other purposes. Generally speaking, the design of the catheter may be similar to conventional catheters except that the catheters are modified to include or incorporate echogenic elements. Exemplary catheters include those described in U.S. Pat. No. 6,350,253 issued Feb. 26, 2002 to Deniega et al. for "Catheter For Uniform Delivery of Medication", the contents of which are incorporated herein by reference.

Referring now to FIG. 4, the echogenic catheter 100 is composed of an elongated tubular member 102 having a proximal end 104, a distal end 106 and an echogenic catheter tip 108 at its distal end 108. The elongated tubular member 102 may be an elongated tubular member 102 with a plurality of exit holes 112 in one or more portions 114 of the elongated tubular member. FIG. 5 illustrates a cross-section of the elongated tubular member 102 taken along line B-B in FIG. 4 illustrating a porous member 116 residing within the tubular member 102. An annular space 118 may be present between the porous member 116 and the elongated tubular member 102. Alternatively, the elongated tubular member 102 may be made of a porous membrane.

Figure 6:
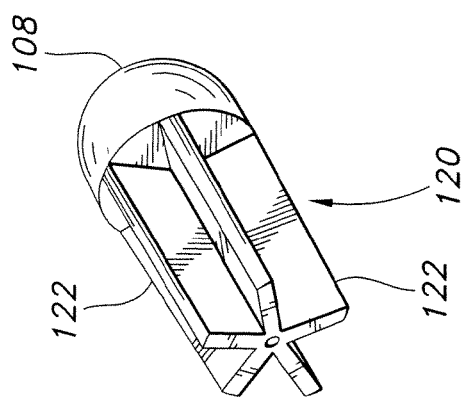
FIG. 6 is an illustration of a detail of an exemplary echogenic catheter showing an exemplary echogenic catheter tip.

The echogenic catheter tip 108 may be a portion of a distal end 106 of the catheter 100 and may be formed from cobalt chrome, glass, quartz, crystalline mineral, or other material having a high degree of acoustic impedance. Another exemplary material may be stainless steel. As shown in FIG. 6, the echogenic catheter tip 108 may include a support 120. The echogenic catheter tip 108 may be formed integrally with the support 120 or may be adhesively bonded thereto. The support 120 may optionally be echogenic. Generally speaking, the echogenic catheter tip 108 may be circular and has a diameter such it is aligned with the outer edges of the ribs 122 of the support 120, as shown.

Figure 7:
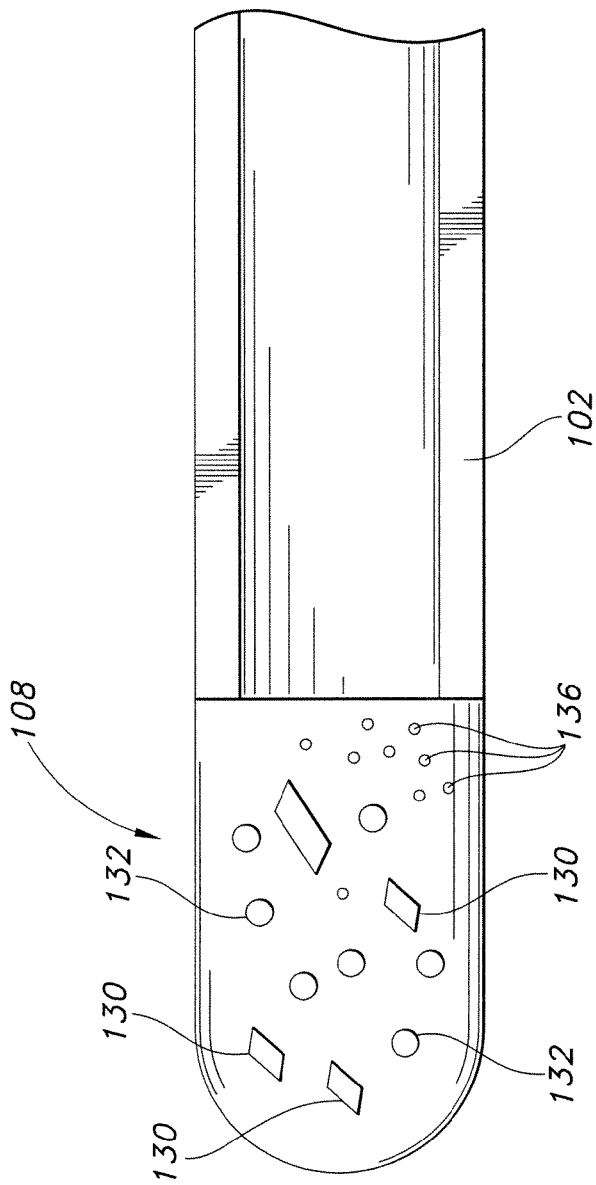
FIG. 7 is an illustration of a detail of an exemplary echogenic catheter including an exemplary echogenic catheter tip.

Referring to FIG. 7, there is shown an embodiment in which the echogenic catheter tip 108 incorporates reflective flakes 130, reflective spheres 132 and/or reflective particles 136 in a carrier matrix 138 of material such as, for example, silicone or other suitable and compatible medical grade plastic that can be used for the catheter tip 108. Exemplary reflective flakes 130 include gold flakes, silver flakes or the like. Reflective spheres 132 include gold spheres, silver spheres, glass spheres or the like. Reflective particles 136 include gold particles, silver particles, glass particles or the like.

Alternatively and/or additionally, the echogenic catheter tip 108 can include a very dense material incorporated into the carrier matrix at a distal location to generate a high degree of impedance mismatch. Dense material could also be incorporated into the tubular member 102 in a distal location to generate a high degree of impedance mismatch.

Appropriate selection of dense materials can create a sufficient level of difference in the acoustic impedance of the tip 108 and/or portion of the elongated tubular member 102 and the acoustic impedance of the surrounding tissue to create a level of reflection that allows visualization of the tip and/or portion of the elongated tubular member 102 utilizing sonic imaging techniques.

One category of relatively dense materials is radio-opaque materials. These materials may be added to the polymer used to make the catheter or the tip. Radio-opaque materials are those that absorb and/or block x-rays from passing through an item. These include iodine and barium substances, bismuth salts, tungsten, gold metal, halogenated moieties, metal containing, optically transparent polymers and mixtures thereof.

Halogenated moieties like halogenated diols and halogenated di-isocyanate reactants may be used to prepare polyurethane that is radio-opaque and desirably visually transparent. It has been found that preparing polyurethane using trans cyclo-hexane 1,4 diisocyanate (t-CHDI) can produce a toxicologically harmless product that is radio-opaque yet visibly transparent. More information on this process may be found in European Patent Application EP 0 523 928 A2 published Jan. 20, 1993 by Wagener et al. for "Kink Resistant, Flexible, Radiopaque Polyurethane Tubing and Catheters Formed Therefrom", the contents of which are incorporated by reference.

The radio-opaque additive may be present in an amount between 5 and 60 weight percent, more desirably 10 and 40 weight percent or still more desirably between 20 and 30 percent. The radio-opaque additive may be compounded with the polymeric material from which the tube is made in the conventional manner; e.g., barium sulfate powder is compounded into the polymer through extrusion compounding to produce resin pellets at the proper weight percent addition rate.

It is contemplated that dense materials may be banded or utilized in segments to provide contrast during sonic imaging. For example, a band or segment may contain little or no radio-opaque additive and another band or segment may contain at least 5 to 10 weight percent more than the section having little or none of the additive. It is also contemplated that both types of bands or segments may contain a radio-opaque material which may be different in type and/or amount, resulting in a different degree of density for the bands or segments (e.g. tungsten in one band or segment and barium sulfate in another band or segment). This differential in density may allow one to discern the locations of the bands or segments utilizing sonic imaging because of differences in acoustic impedance.

Figure 8:
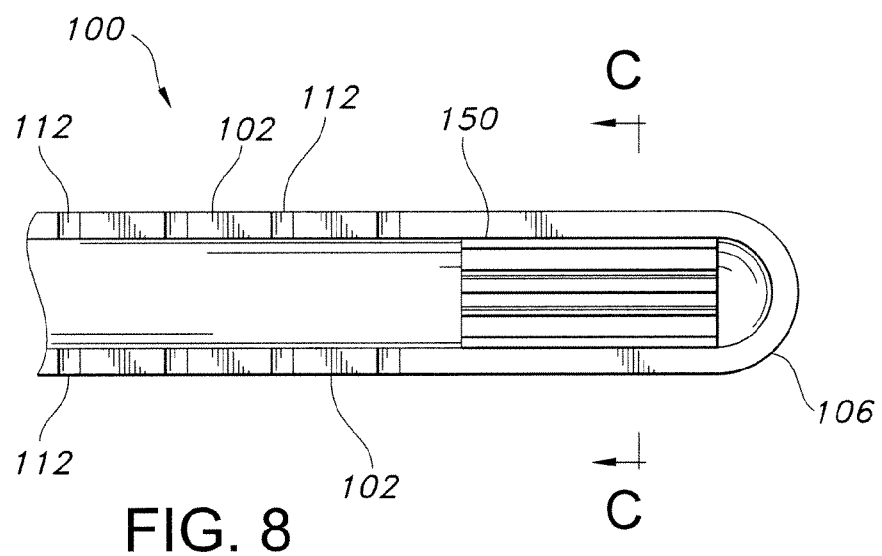
FIG. 8 is an illustration of a detail of an exemplary echogenic catheter showing an exemplary echogenic insert or plug.
Figure 9:
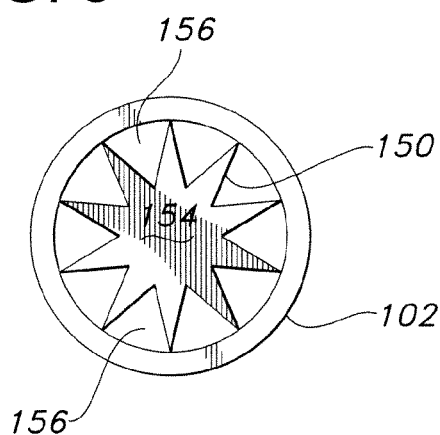
FIG. 9 is an illustration of a cross-section of the exemplary echogenic catheter of FIG. 8 taken across line C-C.

Alternatively and/or additionally, the echogenic catheter tip may be or may include an echogenic insert or plug 120 formed from or coated with cobalt chrome, glass, quartz, crystalline mineral, or other material having a high degree of acoustic impedance. Referring now to FIG. 8, the echogenic catheter 100 may incorporate an echogenic insert or plug 150 having a shape or configuration that reflects an effective amount of acoustic waves so the tip or other portion (or portions) of the catheter incorporating such an insert is visible during sonic imaging. That is, the combination of an appropriate shape or configuration with an echogenic material or echogenic coating is thought to greatly enhance the acoustic reflectivity of the insert or plug. Suitable shapes include gear shapes (e.g., circular or cylindrical shapes having grooves, notches and/or crenulations that provide a plurality of flat reflective surfaces), spherical shapes, multi-faceted geometric shapes formed by interlocking polygons (e.g., a geodesic shape). FIG. 9 illustrates a cross-section of the elongated tubular member 102 taken along line C-C in FIG. 8 illustrating an echogenic insert or plug 150 residing within the tubular member 102. As can be seen in FIG. 9, the echogenic insert or plug 150 has a "star" shaped cross section defined by spines 152 extending radially outward from an axial or core region 154 to define a series of grooves 156 in the echogenic insert 150.

Figure 10:
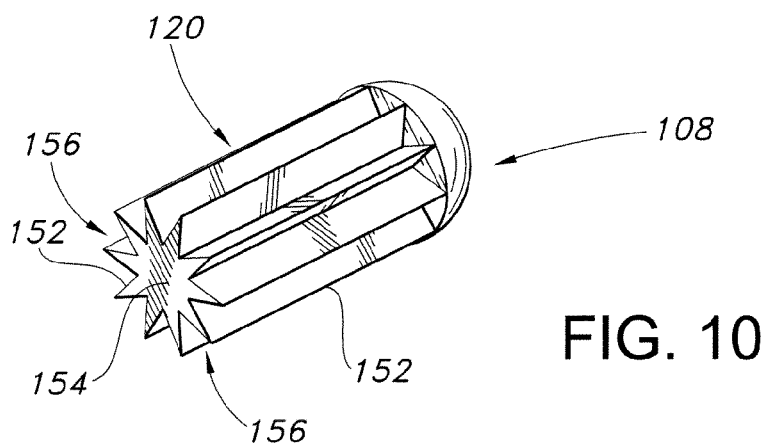
FIG. 10 is an illustration of an exemplary echogenic catheter tip.

FIG. 10 illustrates how such a feature may be incorporated in a catheter tip 108 of the type shown in FIG. 6 such that at least a portion of the catheter tip is echogenic. That is, the catheter tip, the support or both may be echogenic. The catheter tip 108 includes a support 120 that may be formed integrally with the catheter tip or may be adhesively bonded thereto. The support 120 may be generally the same as the illustrated in FIG. 6 except that it is made of or coated with an acoustically reflective material and configured to have a shape that is acoustically reflective. For example, the support may have geometry similar to the echogenic insert illustrated in FIGS. 8 and 9. Referring to FIG. 10, the support 120 has a "star" shaped cross section that may be described spines 152 extending radially outward from an axial or core region 154 to define a series of grooves 156. In other words, the catheter tip may itself be echogenic and/or it may include a support that is echogenic.

Figure 11:
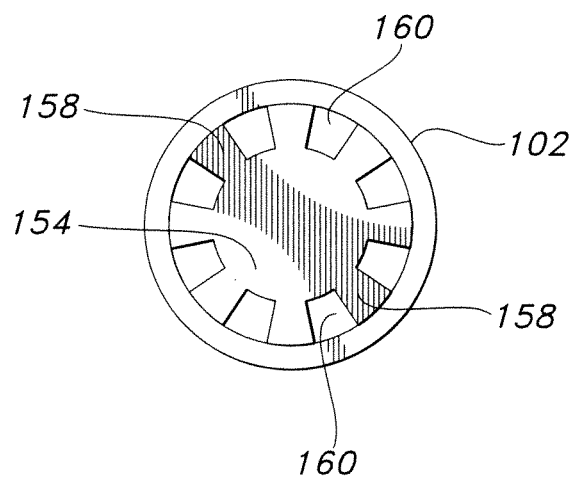
FIG. 11 is an illustration of a cross-section of an exemplary echogenic catheter showing an exemplary echogenic insert or plug.

FIG. 11 illustrates a cross-section of the elongated tubular member 102 taken along line C-C in FIG. 8 illustrating another exemplary echogenic insert or plug 150 residing within the tubular member 102. As can be seen in FIG. 11, the echogenic insert or plug 150 has a "gear" shaped or crenulated cross section defined by protuberances 158 extending radially outward from an axial or core region 154 to define a series of notches 160.

Figure 12A:
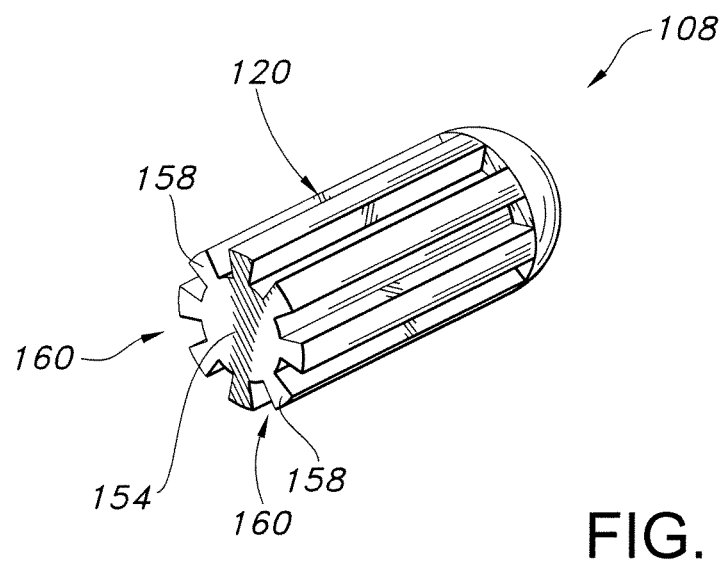
FIG. 12A is an illustration of an exemplary echogenic catheter tip.

FIG. 12A illustrates another example of such a feature incorporated in a catheter tip 108 of the type shown in FIG. 6 such that at least a portion of the catheter tip is echogenic. The catheter tip 108 includes a support 120 that may be formed integrally with the catheter tip or may be adhesively bonded thereto. In this example, the support 120 is generally the same as the echogenic insert illustrated in FIG. 11 and has a "gear" shaped or crenulated cross section defined by protuberances 158 extending radially outward from an axial or core region 154 to define a series of notches 160.

Figure 12B:
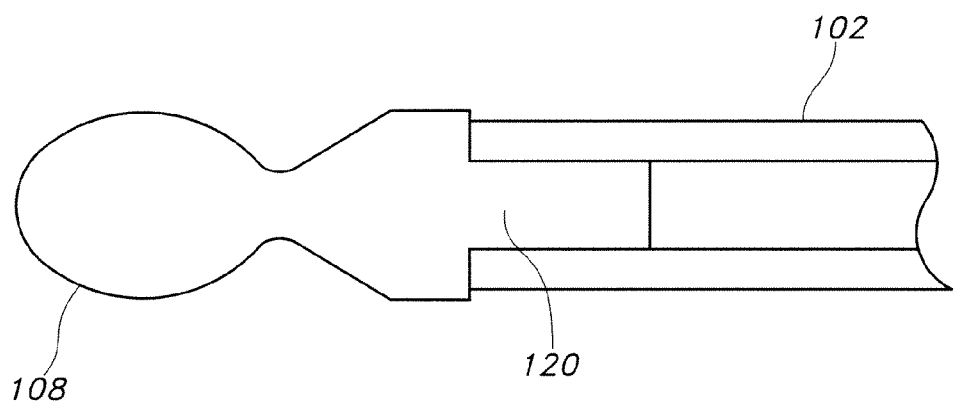
FIG. 12B is an illustration of an exemplary echogenic catheter tip.
Figure 12C:
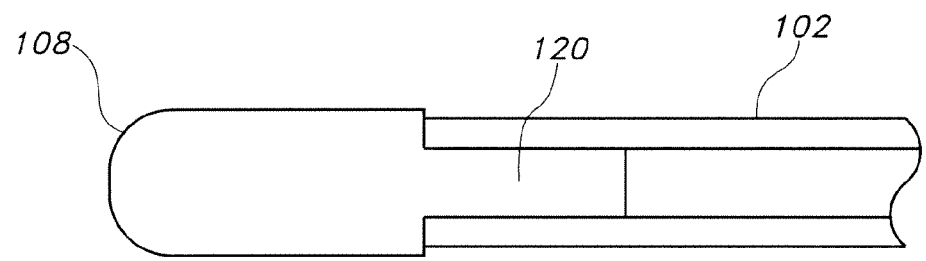
FIG. 12C is an illustration of an exemplary echogenic catheter tip.

FIG. 12B illustrates another exemplary catheter tip 108 that includes a support 120 that may be formed integrally with the catheter tip. The support resides within the tubular member 102 and may be secured by adhesive or by a friction fit or by other mechanical fastening means. This catheter tip has an "hourglass" shape and a surface that is free of crenulations or other complex geometries. FIG. 12C illustrates another exemplary catheter tip 108 that includes a support 120 that may be formed integrally with the catheter tip. The support resides within the tubular member 102 and may be secured by adhesive or by a friction fit or by other mechanical fastening means. This catheter tip has a "bullet" shape and a surface that is free of crenulations or other complex geometries. These relatively simple shapes are desirably made of stainless steel but other materials having a high degree of acoustic impedance may be used including, but not limited to cobalt chrome, glass, or quartz.

As generally illustrated in FIGS. 8, 9 and 11, the sharp and/or flat edges of the echogenic insert (or support) may engage the walls of the lumen defined by the elongated tubular member 102 to prevent the echogenic insert (or the echogenic catheter tip) from moving relative to the elongated tubular member.

Alternatively and with reference to FIG. 13A, the echogenic catheter 100 may incorporate an echogenic insert or plug 150 within the elongated tubular member 102. The echogenic insert or plug 150 may be made of glass, quartz crystal or similar material and has a generally cylindrical shape or configuration and which includes one or more tubes or cylindrical channels 170 that passes through the material to create a density difference that is visible using sonic imaging. FIG. 13B is a cross-sectional view of the echogenic catheter shown in FIG. 13A taken along line D-D. As illustrated in FIG. 13B, the tubular member 102 incorporates an echogenic insert 150 having a cylindrical cross section and one or more tubes or cylindrical channels 170 that passes through the material to create a density difference that is visible using sonic imaging.

In an aspect of the invention, the echogenic catheter 100 may incorporate an echogenic bead 172 having a spherical or spheroid shape within the elongated tubular member 102 as illustrated in FIG. 14A. The echogenic bead 172 may be made of glass, quartz crystal or similar material or may be made of any conventional non-echogenic material and provided with an echogenic coating. The echogenic bead has a plurality of dimples 174 and may further include rugosities or wrinkles to enhance visibility using sonic imaging. FIG. 14B is a perspective view showing a detail of the echogenic bead 172 highlighting the dimples and rugosities.

FIG. 15A is a cross-sectional view of an exemplary echogenic catheter 100 illustrating voids or bubbles 176 formed in the elongated tubular member 102. These voids or bubbles are generated during manufacture of the catheter. The voids or bubbles may be created by introducing a gas into the polymer that is extruded to form the catheter. The voids or bubbles may also be created by the extrusion process, by mixing a gas generating material with the polymer or by other conventional techniques. Desirably, the voids or bubbles 176 are present in the material of the elongated tubular member 102 as illustrated in FIG. 15B and are not present at the surface of the elongated tubular member. It is generally thought that the voids or bubbles in the polymer material can provide sufficiently high degree of impedance mismatch to allow visualization through sonic imaging. It is contemplated that materials may be mixed with the polymer to increase the density of the polymer to further enhance the degree of impedance mismatch. Exemplary materials are described above and may include radio-opaque materials.

FIG. 16A is an illustration of an elongated tubular member 102 of an echogenic catheter 100 incorporating at its distal end 106 an echogenic catheter tip 108 having a shaft 180. The catheter tip 108 may be made echogenic generally as described above or it may further include bands 182 of an echogenic material. It is contemplated that the bands may be glass, quarts or other echogenic material. It is also contemplated that the bands may be a material having a high degree of impedance mismatch to allow visualization through sonic imaging. FIG. 16B illustrates a detail of the echogenic catheter tip 108 having a shaft 180 that incorporates a band or insert 182 of an echogenic material or a material having a high degree of impedance mismatch to allow visualization through sonic imaging.

According to an aspect of the invention, the catheter 100 may incorporate a metal spring 190 within the elongated tubular member 102. Generally speaking, the metal spring 190 may be used to provide kink-resistance. The metal spring 190 may be modified to enhance its acoustic impedance. The can be accomplished by changing the generally round cross-section 192 of the metal spring 190 as illustrated in FIG. 17B into a generally flat cross-section 194 as illustrated in FIG. 17C. This generally flat cross-section 194 may be provided in portions or alternating regions of the metal spring and/or it may be located at the distal end 106 of the catheter. It is contemplated that the metal spring 190 may be made actively echogenic by being connected to a transducer that vibrates the spring at a frequency sufficient to generate acoustic waves that are visible through sonic imaging. Such a transducer may be, for example a piezoelectric transducer. Other types of transducers may include magnetostrictive transducers, electromagnetic transducers, or laser-activated elements may be used.

The catheter 100 may be made echogenic by incorporating a removable echogenic guide wire 200 in the catheter. The guide wire 200 may be echogenic because it is formed it out of an echogenic material or because of an applied echogenic coating. Alternatively and/or additionally, an echogenic guide wire tip 202 may be added to the echogenic guide wire 200. It is contemplated that the guide wire 200 may include a strand or additional wire 204 that is formed it out of an echogenic material, contains an applied echogenic coating such that it is passively echogenic. The strand or additional wire may be configured to vibrate due to a connection with a transducer.

Catheters frequently are manufactured with one or more metal band or rings. In an aspect of the invention, such metal bands or rings may be modified so they are echogenic. Referring to FIG. 19, there is shown an illustration of an exemplary catheter 100 having a plurality of exit holes 112 and which incorporates a first metal band 250 near the distal end 106 of the catheter and a second metal band 252. Referring to FIGS. 19 and 20, the bands may have a cross section that may be described as defining spines, protuberances, crenels or the like 254 extending radially outward from the elongated tubular member 102. It should be noted that the protuberances 254 are recessed in the catheter so they do not protrude beyond outermost radial surface of the elongated tubular member 102. Alternatively and/or additionally, the metal bands may include grooves, indentations, cross-hatching or the like to enhance visualization by sonic imaging techniques.

In an aspect of the invention, the metal band or metal bands and/or any echogenic component(s) of the catheter may be configured to provide information about the catheter. Desirably, that information is provided during sonic imaging and is interpreted based on the intensity or placement (or combinations thereof) of the echogenic components. In another aspect of the invention, one or more chart(s) or other tool(s) may be provided to allow others (e.g., medical professionals) to interpret the information. Alternatively and/or additionally, the image provided during sonic imaging may be interpreted by the sonic imaging equipment. Examples of information about the catheter that may be provided include, but are not limited to, exit hole placement, exit hole density, length, diameter (or other size information), whether the catheter has an open tip, whether the catheter has a closed tip, and the like.

The elongated tubular member 102 of the catheter 100 may be rendered echogenic by coating an internal or external surface with a material that increases its acoustic impedance. Exemplary materials include titanium carbide, titanium nitride, titanium aluminum nitride, titanium aluminum carbon nitride or similar materials. Hard, dense, amorphous non-crystalline solids such as glass, acrylic glass—also referred to as poly(methyl methacrylate, and hard, glassy hydrogels such as those described in US Patent Application Publication No. US 2006/0141186 published Jun. 29, 2006 by Janssen et al. for "Gloves With Hydrogel Coating For Damp Hand Donning and Method of Making Same" may also be used.

The coating may be on the outside of the elongated tubular member or the coating may be located on the interior of the elongated tubular member. In some aspects of the invention, the coating on the interior of the elongated tubular member may be a coating that incorporates acoustically reflective particles in a carrier. For example, the coating may include spherical beads of glass or other acoustically reflective material in a carrier that binds spherical beads to an internal surface of the elongated tubular member.

Alternatively and/or additionally, the elongated tubular member (and/or the catheter tip) may be rendered echogenic with various known echogenic coatings such as described in U.S. Pat. No. 6,506,156 issued Jan. 14, 2003 to Jones et al.; U.S. Pat. No. 7,229,413, issued Jun. 12, 2007 to Violante et al.; and in U.S. Patent Application Publication No. US 2009/0318746 A1, published Dec. 24, 2009 to Thurmond, II et al., the contents of which are incorporated by reference. According to another aspect of the invention, the elongated tubular member of the catheter may be rendered echogenic by including an internal component that increases its acoustic impedance. The internal component may be an echogenic metal wire or even an elongated tubular coil spring enclosed within the tubular member. The elongated tubular coil spring may be may formed from an echogenic material, may be coated with a material that increases its acoustic impedance, or may have a surface that is modified with grooves, diffraction gratings, dimples or the like to increase its acoustic impedance.

Alternatively and/or additionally, the internal component may be a component that actively generates acoustic waves visible during sonic imaging. Such a component may include an energy source or may be connected to an energy source and may further include a transducer such as, for example a piezoelectric transducer that converts the energy into acoustic waves. Other types of transducers including magnetostrictive transducers, electromagnetic transducers, or laser-activated elements may be used.

In embodiments where the elongated tubular member is an elongated tube with a plurality of exit holes or slots in a portion of the elongated tube and an elongated porous member resides within the tube, it is contemplated that the elongated porous member may be made of or may include material that increases its acoustic impedance. Examples include porous composites that may include spherical beads of glass or other acoustically reflective material, batts or webs formed of thermoplastic polymer fibers having entrapped along the length thereof bubbles of a gas, a porous matrix composed of a polymer network having gas filled closed cells distributed in the matrix, or similar structures. An example of a batt or web formed of thermoplastic polymer fibers having entrapped along the length thereof bubbles of a gas can be founding U.S. Pat. No. 6,395,215 issued May 28, 2002 to Jameson for "Method and Apparatus for Ultrasonically Assisted Melt Extrusion of Fibers", the contents of which is incorporated herein by reference. An example of a porous matrix composed of a polymer network having gas filled closed cells distributed in the matrix, or similar structures can be found in U.S. Pat. No. 7,160,553 issued Jan. 9, 2007 to Gibbins et al. for "Matrix for Oxygen Deliver to Compromised Tissues", the contents of which is incorporated herein by reference.

The present invention encompasses an apparatus for performing a nerve block procedure. The apparatus is composed of an echogenic needle as described above and an echogenic catheter configured for controlled delivery of a medication as described above. The apparatus may further include an echogenic sheath. Exemplary echogenic sheaths are described in U.S. Patent Application Publication No. US 2009/0005774 A1, published Jan. 1, 2009 to Fernald, the contents of which are incorporated by reference. Such an echogenic sheath may be rendered echogenic by any of the above described materials or techniques or combinations thereof. It may, however, be desirable to also render the sheath echogenic to aid in the guidance procedure and to ultrasonically verify placement of the sheath after removal of the needle. In this regard, the sheath may contain any manner echogenic material, such as metal threads or flakes, formed with the sheath or subsequently added to the surface of the sheath. In another embodiment, the sheath may be rendered effectively echogenic by simply defining holes or perforations through the sheath such that that the metal needle is exposed through the perforations during the ultrasonically imaging. By detecting axial points or sections of the needle through the sheath, the location of the sheath is also verified.

The present invention also encompasses a system for performing a nerve block procedure. The system includes introducing an echogenic needle as described above in the general area of a nerve bundle, positioning the echogenic needle adjacent the nerve bundle utilizing sonic imaging techniques, introducing an echogenic catheter configured for controlled delivery of a fluid as described above through the echogenic needle, withdrawing the echogenic needle, positioning the echogenic catheter adjacent the nerve bundle utilizing sonic imaging techniques, and delivering fluid to the nerve bundle through the echogenic catheter.

The above-described system for performing a new block procedure may further include the steps of placing a sheath over the echogenic needle prior to introducing the echogenic needle adjacent the general area of the nerve bundle and withdrawing the echogenic needle while maintaining the sheath in place and then advancing the echogenic catheter through the sheath. The sheath may be an echogenic as generally described above.

The present invention also encompasses another apparatus for performing a nerve block procedure. This apparatus includes an echogenic soft tissue tunneling device for creating a subcutaneous path for placement of a catheter in a patient and an echogenic catheter configured for controlled delivery of a medication.

Exemplary soft tissue tunneling devices are described at, for example, U.S. Patent Application Publication No. US 2008/0086161 A1 for "Soft Tissue Tunneling Device" published Apr. 10, 2008 by Massengale et al.; and U.S. Patent Application Publication No. US 2008/0312677 A1 for "Soft Tissue Tunneling Device" published Dec. 18, 2008 by Massengale et al.; the entire contents of each is incorporated herein by reference.

For example, these soft tissue tunneling devices include an elongate shaft having a rounded distal end. The distal end and/or the elongate shaft may be made echogenic in a manner similar to the echogenic needle and/or catheter as described above. These devices may further include a handle secured to the shaft in which the handle is configured to permit a user of the tunneling device to manually manipulate the tunneling device. The elongate shaft may be malleable so as to permit a shape of the shaft to be altered prior to use of the tunneling device. For example, the shaft may have a non-linear shape including, but not limited to, a curved shape.

The apparatus further includes a sheath positionable over a portion of the shaft. The sheath has a snug fit with the shaft such that the sheath and the shaft can be advanced together and positioned within a body of a patient. According to the invention, at least one of the elongate shaft and sheath are echogenic. That is, the elongate shaft of the tissue tunneling device may be echogenic, the sheath may be echogenic, or both may be echogenic.

According to an aspect of the apparatus for performing a nerve block procedure, the elongate shaft of the echogenic soft tissue tunneling device may define an interior lumen. In addition, the tunneling device may include at least one fluid exit opening positioned along the length of the shaft and extending from the interior lumen to an external surface of the shaft, and an inlet to the interior lumen to permit liquid to be introduced into the interior lumen and administered to the patient through the at least one fluid exit opening. The apparatus may further include a sheath slidably positioned on the elongate shaft such that at least one of the elongate shaft and sheath is echogenic In another aspect of the invention, the tunneling device may further include a retractable needle located at the distal end of the elongate shaft. The retractable needle can be used to assist in puncturing the skin prior to advancing the tunneling device within the patient's body. The retractable needle can be housed within the distal end of a needle lumen, and may be fully retracted within the needle lumen so that the elongate shaft maintains a substantially blunt distal end. The position of the retractable needle within the needle lumen may be changed using any suitable method.

The present invention also encompasses a system for performing a nerve block procedure utilizing the echogenic soft tissue tunneling device described above. Generally speaking, the system includes the steps of: (i) grasping the handle of an echogenic soft tissue tunneling device for creating a subcutaneous path for placement of a catheter in a patient—in which the tunneling device includes an elongate shaft having a rounded distal end and defining at least one interior lumen and at least one fluid exit opening in fluid communication with the interior lumen; (ii) introducing the echogenic tunneling device into the body of a patient in the general area of a nerve bundle; (iii) positioning the echogenic tunneling device adjacent the nerve bundle utilizing sonic imaging techniques; (iv) withdrawing the echogenic tunneling device; (v) introducing an echogenic catheter configured for controlled delivery of a fluid through the subcutaneous path created by the echogenic tunneling device; (vi) positioning the echogenic catheter adjacent the nerve bundle utilizing sonic imaging techniques, and (vii) delivering fluid to the nerve bundle through the echogenic catheter.

In an aspect of the system, the echogenic tunneling device may further include a sheath that slidably surrounds a portion of the shaft, such that the system further includes the steps of (a) introducing and advancing the sheath along with the introducing and positioning of the tunneling device, and (b) withdrawing the shaft from the sheath and leaving the sheath within the body. When such a sheath is utilized in the system, at least one of the tunneling device and the sheath should be echogenic.

While various patents have been incorporated herein by reference, to the extent there is any inconsistency between incorporated material and that of the written specification, the written specification shall control. In addition, while the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

What is claimed is:

1. An apparatus for performing a nerve block procedure, the apparatus comprising an echogenic needle and an echogenic catheter insertable through the echogenic needle and configured for controlled delivery of a medication, the echogenic catheter comprising an elongated tubular member having walls and an echogenic catheter tip, the echogenic catheter tip comprising one of: an echogenic insert entirely within the tubular member or; an echogenic plug including a support that resides within the tubular member, the echogenic insert and echogenic plug having a shape that reflects an effective amount of acoustic waves so the catheter tip is satisfactorily visible during sonic imaging, the shape being selected from gear shapes, hourglass shapes, hemisphere-terminated cylinder shapes, and multi-faceted geometric shapes formed by interlocking polygons, the echogenic insert and the echogenic plug having edges that engage the walls of the tubular member to prevent the echogenic insert and echogenic plug from moving relative to the elongated tubular member, wherein the edges and the walls of the tubular member, when engaged, define a plurality of grooves or notches between the edges and the walls of the tubular member.

2. The apparatus of claim 1, wherein the echogenic needle has a distal end composed of an echogenic needle tip, a hollow needle body, and a proximal end that includes a fitting.

3. The apparatus of claim 2, wherein the needle body is an echogenic needle body.

4. The apparatus of claim 3, wherein at least a portion of the needle tip and/or needle body incorporates or is coated with a material that increases acoustic impedance.

5. The apparatus of claim 4, wherein the material is from the group consisting of titanium carbide, titanium nitride, titanium aluminum nitride, and titanium aluminum carbon nitride.

6. The apparatus of claim 4, wherein the material is a hard, dense, amorphous non-crystalline solid.

7. The apparatus of claim 6, wherein the material is selected from glass, poly(methyl methacrylate), and hard, glassy hydrogels.

8. The apparatus of claim 1, wherein the echogenic catheter tip is formed from or coated with cobalt chrome, glass, or other material having a high degree of acoustic impedance.

9. The apparatus of claim 1, further comprising an echogenic sheath.

10. An echogenic catheter configured for controlled delivery of a fluid across an anatomical region, the echogenic catheter comprising:
   an elongated tubular member having walls, and
   an echogenic catheter tip comprising one of an echogenic insert entirely within the tubular member or; an echogenic plug including a support that resides within the tubular member, the echogenic plug and echogenic insert having a shape that reflects an effective amount of acoustic waves so the tip is satisfactorily visible during sonic imaging, the shape being selected from gear shapes, hourglass shapes, hemisphere-terminated cylinder shapes, and multi-faceted geometric shapes formed by interlocking polygons, the echogenic insert and the echogenic plug having edges that engage the walls of the tubular member to prevent the echogenic insert and echogenic plug from moving relative to the elongated tubular member, wherein the edges and the walls of the tubular member, when engaged, define a plurality of grooves or notches between the edges and the walls of the tubular member.

11. The echogenic catheter of claim 10, wherein the echogenic catheter tip is formed from or coated with cobalt chrome, glass, or other material having a high degree of acoustic impedance.

* * * * *